United States Patent
Park et al.

(10) Patent No.: US 11,169,066 B2
(45) Date of Patent: Nov. 9, 2021

(54) METHOD FOR QUANTITATIVE ANALYSIS OF POLYMER STRUCTURE AND ANALYZER

(71) Applicant: LG Chem, Ltd., Seoul (KR)

(72) Inventors: Sung Hyun Park, Daejeon (KR); Chae Gyu Lee, Daejeon (KR); Ye Hoon Im, Daejeon (KR); Yu Taek Sung, Daejeon (KR); Myung Han Lee, Daejeon (KR); Oh Joo Kwon, Daejeon (KR); Heon Yong Kwon, Daejeon (KR); Dae Sik Hong, Daejeon (KR)

(73) Assignee: LG Chem, Ltd.

( * ) Notice: Subject to any disclaimer, the term of this patent is extended or adjusted under 35 U.S.C. 154(b) by 815 days.

(21) Appl. No.: 15/767,519

(22) PCT Filed: Mar. 30, 2017

(86) PCT No.: PCT/KR2017/003455
§ 371 (c)(1),
(2) Date: Apr. 11, 2018

(87) PCT Pub. No.: WO2017/171416
PCT Pub. Date: Oct. 5, 2017

(65) Prior Publication Data
US 2018/0306694 A1    Oct. 25, 2018

(30) Foreign Application Priority Data
Mar. 31, 2016    (KR) .................. 10-2016-0038881

(51) Int. Cl.
*G01N 11/00*    (2006.01)
*G16C 20/00*    (2019.01)
(Continued)

(52) U.S. Cl.
CPC .......... *G01N 11/00* (2013.01); *G01N 33/442* (2013.01); *G16C 20/00* (2019.02); *G16C 60/00* (2019.02);
(Continued)

(58) Field of Classification Search
None
See application file for complete search history.

(56) References Cited

U.S. PATENT DOCUMENTS

2005/0037232 A1 * 2/2005 Tyan .................... H01L 51/5265
428/690
2005/0085598 A1 * 4/2005 Sandell ................ B01J 19/0006
526/64
(Continued)

FOREIGN PATENT DOCUMENTS

| JP | H10326272 A | 12/1998 |
| KR | 100829706 B1 | 5/2008 |

(Continued)

OTHER PUBLICATIONS

Search report from International Application No. PCT/KR2017/003455, dated Jul. 7, 2017.
(Continued)

*Primary Examiner* — Eric S. McCall
*Assistant Examiner* — Mohammed E Keramet-Amircolai
(74) *Attorney, Agent, or Firm* — Lerner, David, Littenberg, Krumholz & Mentlik, LLP

(57) ABSTRACT

The present application relates to a method for quantitative analysis of a polymer structure. Specifically, the method may be carried out through steps of measuring rheological properties and/or molecular weight distribution of the arbitrarily selected polymer, setting a random value for the selected polymer and then predicting the rheological property and/or the molecular weight distribution of the polymer
(Continued)

from the random value, and comparing the measured value with the predicted value to determine the value of the structural parameter of the polymer.

15 Claims, 3 Drawing Sheets

(51) Int. Cl.
*G16C 60/00* (2019.01)
*G01N 33/44* (2006.01)
*G01N 24/08* (2006.01)

(52) U.S. Cl.
CPC ........ *G01N 24/08* (2013.01); *G01N 2011/004* (2013.01)

(56) References Cited

U.S. PATENT DOCUMENTS

| | | | | |
|---|---|---|---|---|
| 2009/0304705 | A1* | 12/2009 | Grass | C12Q 1/6883 424/144.1 |
| 2014/0214338 | A1* | 7/2014 | Lee | G16C 20/20 702/27 |
| 2014/0297239 | A1* | 10/2014 | Ueno | G16C 20/30 703/2 |
| 2015/0353659 | A1* | 12/2015 | Atiqullah | C08F 210/16 524/855 |
| 2016/0159981 | A1* | 6/2016 | Haynie | C09D 177/04 521/183 |
| 2017/0081466 | A1* | 3/2017 | Kornfield | C08K 11/00 |
| 2018/0258230 | A1* | 9/2018 | Grubbs | C08F 285/00 |
| 2018/0306694 | A1* | 10/2018 | Park | G16C 60/00 |
| 2019/0284317 | A1* | 9/2019 | Kwon | C08J 5/18 |

FOREIGN PATENT DOCUMENTS

| | | |
|---|---|---|
| KR | 101340739 B1 | 1/2014 |
| KR | 20140095089 A | 7/2014 |

OTHER PUBLICATIONS

Lee, Young Sil, et al., "Determination of Molecular Weight and Molecular Weight Distribution of Polypropylene Using Rheological Properties." Polymer(korea), Vo. 38, No. 6 (Received Mar. 25, 2014; Revised May 19, 2014; Accepted May 29, 2014) pp. 735-743.
Extended European Search Report including Written Opinion for Application No. EP 17 77 5840 dated Mar. 14, 2019.
Larson R G: "Combinatorial Rheology of Branched Polymer Melts", Macromolecules, American Chemical Society, US, vol. 34, No. 13, May 25, 2001 (May 25, 2001), pp. 4556-4571, XP001133769.

* cited by examiner

[Figure 1]
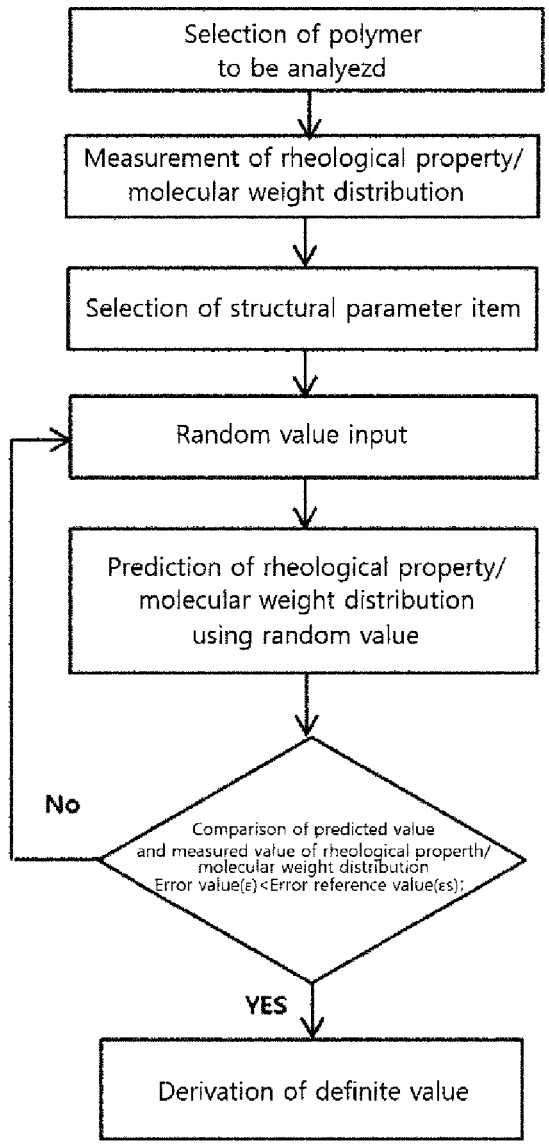

[Figure 2]
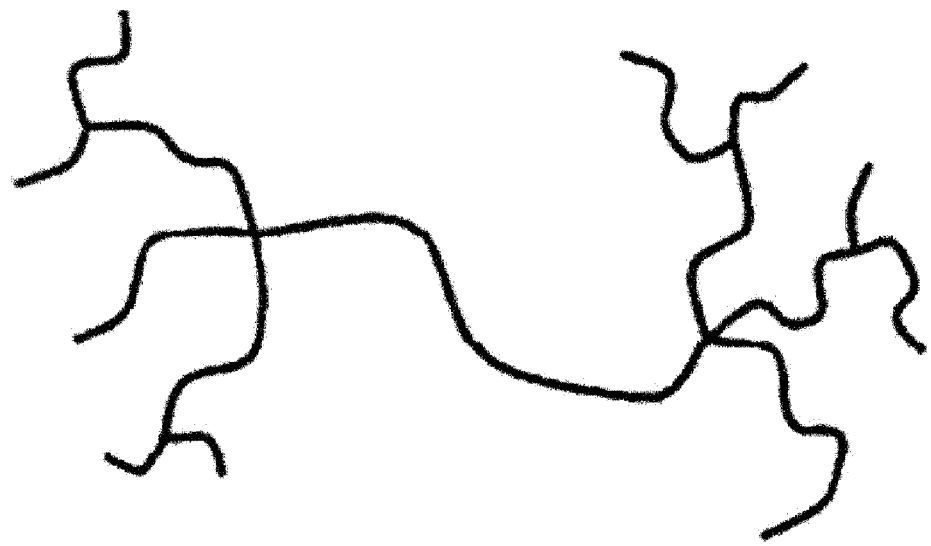
Pom-Pom Polymer
[Figure 3]
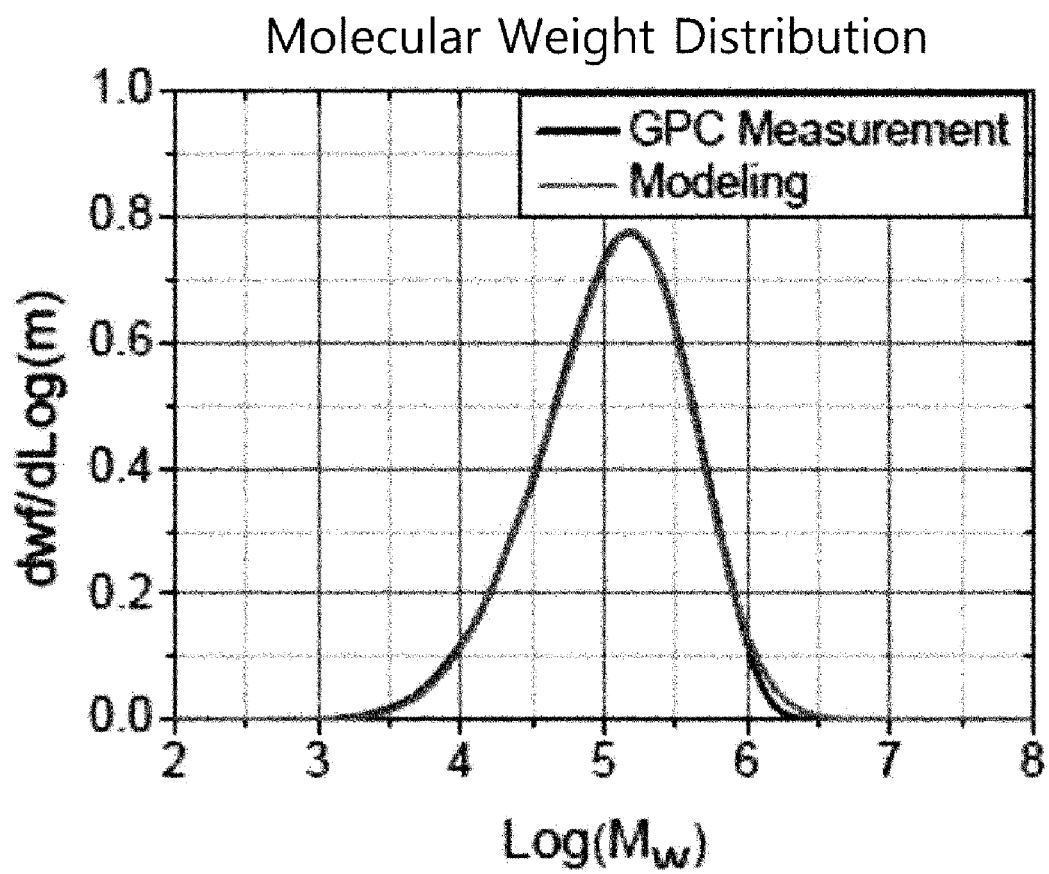

[Figure 4]
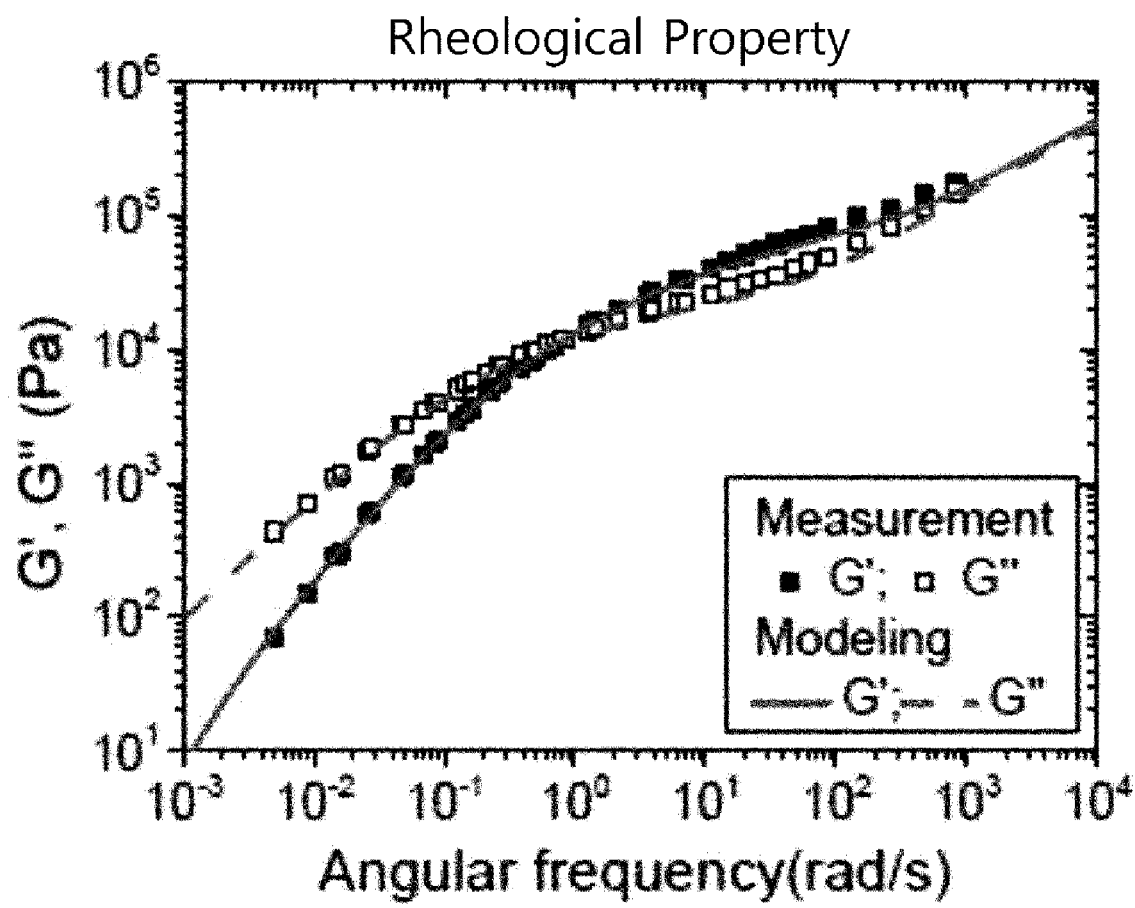

METHOD FOR QUANTITATIVE ANALYSIS OF POLYMER STRUCTURE AND ANALYZER

CROSS-REFERENCE TO RELATED APPLICATIONS

The present application is a national phase entry under 35 U.S.C. § 371 of International Application No. PCT/KR2017/003455 filed on Mar. 30, 2017, which claims the benefit of priority based on Korean Patent Application No. 10-2016-0038881 filed on Mar. 31, 2016, the disclosure of which is incorporated herein by reference in its entirety.

TECHNICAL FIELD

The present application relates to a method for quantitative analysis of polymer structure and an analyzer.

BACKGROUND ART

Generally, a polymer is classified into a linear polymer or a branched polymer according to its shape. The linear polymer designates as the word a shape in which monomers constituting the polymer are linearly bonded to form a main chain. Various kinds of chains are branched for such a linear polymer, so that the polymer may have side chains. The polymer structure having such side chains is referred to as a branched polymer and such a branched polymer has physical properties of polymers that differ greatly depending on the molecular weight, distribution and number of the side chains. In this way, it is important in analyzing polymer characteristics to identify the existence of side chains that have a great influence on the physical properties of polymers and to accurately measure the structures thereof.

As the existing method for analysis of side chains, GPC column analysis and NMR analysis were used.

The GPC column analysis uses a method of comparing the viscosity of a branched polymer passing through a GPC column to the viscosity of a linear polymer having the same molecular weight or a method of comparing the radius of gyration of a branched polymer passing through a GPC column to the radius of gyration of a linear polymer using light scattering, and the like, but these methods can be analyzed only for the components having a weight average molecular weight of 100,000 or more due to the sensitivity limitation of the analyzing equipment, so that there is a problem that the analysis is difficult for the weight average molecular weight of less than 100,000.

Furthermore, although the NMR analysis can discriminate the length of side chains having 6 or less carbon atoms, there is a problem that it is difficult to determine the length of side chains having 7 or more carbon atoms. In particular, considering the fact that the weight average molecular weight of the side chains affecting rheological properties is usually 1000 or more, the NMR analysis has a problem that it is not known whether the side chain determined to have a carbon number of 7 or more affecting the rheological properties is a long chain branch or a short chain branch.

The present invention is intended to provide a method for analysis of a polymer structure capable of quantitatively analyzing a polymer structure by repeating a process of predicting rheological properties and/or molecular weight distribution from structural parameters of the polymer and comparing them with the measured values. Moreover, in the case of a polymer mixture, it is intended to provide a method for analysis of a polymer structure capable of quantitatively analyzing the structure and content ratio of each polymer in the mixture.

DISCLOSURE

Technical Problem

It is the object of the present invention to provide a method for quantitative analysis of a polymer structure which predicts rheological properties and/or molecular weight distribution of a polymer and compares them with the measured values to determine polymer structural parameter values.

Technical Solution

In one example regarding the present application, the present application relates to a method for quantitative analysis of a polymer structure. The method for quantitative analysis of a polymer structure in the present application may comprise steps of:

(A) measuring rheological properties of a polymer;

(B) selecting any one of structural parameters that the polymer may have, and assigning a random value to the selected structural parameter; and (C) predicting the rheological property of the polymer to which the random value is assigned and comparing the predicted rheological property value of the polymer with the measured rheological property value of the polymer to determine the value of the structural parameter of the polymer.

In another example regarding the present application, the method for quantitative analysis of a polymer structure may further comprise, in the step (C), a step of predicting the molecular weight distribution of the polymer to which the random value is assigned and comparing the predicted molecular weight distribution value of the polymer with the measured molecular weight distribution value of the polymer to determine the value of the structural parameter of the polymer.

Advantageous Effects

The polymer structure analysis method according to the present application may determine polymer structural parameter values by comparing the measured values and the predicted values of the rheological properties and/or the molecular weight distribution of a polymer having a weight average molecular weight of 100,000 or less and a carbon number in the side chain of 7 or more.

BRIEF DESCRIPTION OF DRAWINGS

FIG. 1 is a flowchart of a quantitative analysis method of a polymer structure of the present invention.

FIG. 2 is a Pom-Pom polymer. The Pom-Pom model is a model in which a branched polymer structure is assumed as a polymer having a plurality of side chains at both ends of one main chain.

FIG. 3 is a graph showing the molecular weight distribution of a predicted value of the structural parameter of the polymer mixture and measured value of the structural parameter of the polymer mixture.

FIG. 4 is a graph showing the rheological property of a predicted value of the structural parameter of the polymer mixture and measured value of the structural parameter of the polymer mixture.

BEST MODE

The present invention relates to a quantitative analysis method of a polymer structure, a computer readable recording medium containing a program capable of carrying out the method, and an analyzer capable of performing the method.

The polymer structure quantitative analysis method of the present application can determine structural parameter values of the arbitrarily selected polymer by predicting rheological properties or molecular weight distribution of the polymer from random values of structural parameters of the arbitrarily selected polymer, for example, weight average molecular weights of the main chain or side chains, polydispersity indexes or numbers of side chains, and comparing them with the measured values of the rheological properties or molecular weight distribution. The analysis method according to the present application not only solves the problem that the object to be measured has a weight average molecular weight of 100,000 or more, or the carbon number of the side chain is limited to 6 or less, in the conventional GPC column analysis method or NMR analysis method, but also can analyze the structural parameters of the polymer quantitatively, even if only the rheological properties and/or molecular weight distribution of the polymer are measured, and moreover, can analyze the structure and the content ratio of each polymer in the polymer mixture.

Hereinafter, the polymer structure quantitative analysis method of the present application will be described in detail.

In one example regarding the present application, the present application relates to a method for quantitative analysis of a polymer structure. The analysis method provides a method for quantitative analysis of a polymer structure comprising steps of:

(A) measuring rheological properties of the polymer;

(B) selecting one or more parameters among structural parameters that the polymer may have, and assigning random values to the selected structural parameters; and (C) predicting rheological properties of the polymer to which the random values are assigned, and comparing the predicted rheological property values of the polymer with the measured rheological property values of the polymer to determine the structural parameter values of the polymer.

The step (a) may be a step of arbitrarily selecting a polymer to be analyzed, and measuring rheological properties of the selected polymer.

In one example, in step (a), the rheological properties of the selected polymer can be measured using a rheometer. The rheometer is not particularly limited as long as it is a device capable of measuring rheological properties, and for example, a rotational rheometer can be used. The rotational rheometer can measure, for example, shear storage elastic modulus (G'), shear loss elastic modulus (G") and shear complex viscosity ($\eta^*$).

The polymer selected in the step (a) may be at least one selected from the group consisting of a linear polymer, a branched polymer, a linear polymer mixture and a branched polymer mixture.

In one example, the linear polymer mixture may be a mixture in which linear polymers having different structural parameters are mixed by physical force, and the branched polymer mixture may be a mixture in which polymers having different structural parameters are mixed by physical force. In another example, the mixed polymer is a polymer having identical constituent elements to each other, but may be a polymer having a different shape such as a linear or branched shape.

In one example, the branched polymer may be a polymer having a weight average molecular weight ratio of side chains to the main chain of 40% or less, or having a weight average molecular weight in only the side chains of 3,000 or more. When the weight average molecular weight ratio of the side chain to the main chain is more than 40%, the analytical reliability of the branched polymer may deteriorate because the side chain may act as a part of the main chain other than the side chain depending on the position occupied in the main chain. Furthermore, when the weight average molecular weight of the side chain in the branched polymer is less than 3,000, the difference in the rheological properties of the polymer due to the side chain is insignificant, so that the use of the analysis method using the difference of rheological properties may be limited as the quantitative analysis method of the polymer structure of the present application.

In the step (b), the selected structural parameters may be one or more selected from the group consisting of a polymer shape; a weight average molecular weight (Mw) of the main chain or side chain; a polydispersity index (PDI) of the main chain or side chain; and a number of side chains.

The polymer shape parameter is a parameter capable of distinguishing whether the polymer to be analyzed is a linear or branched polymer and specifically, represents a parameter capable of qualitatively distinguishing the branched polymer which can appear as a comblike shape, a star shape or an H-shape depending on the side chains bonded to the branched polymer.

Also, in the step (b), the random value can be usually assigned without particular limitation within a numerical range possible as structural parameter values. For example, when the selected structural parameter of the polymer is polydispersity index, a value of 1 to 10 can be assigned as a random value.

In one example, when the polymer selected in the step (a) is a polymer mixture, the structural parameters may further include a mass fraction between the mixed polymers. By including the mass fraction in the parameters, the structure and content ratio of each component in the polymer mixture can be quantitatively analyzed. For example, the weight average molecular weight and polydispersity index parameters of each polymer in the polymer mixture can be calculated by a multiplication method with the mass fraction parameter to be applied to the prediction of the rheological properties and/or molecular weight distribution in the step (c).

In the step (c), a step strain of a shear flow is applied to the polymer to which the random value is assigned, where the rheological properties can be predicted from a stress relaxation behavior of the polymer induced by the step strain. The stress relaxation behavior may vary by the lengths of the main chain and side chains of the polymer, the molecular weight distribution, and the hierarchical structure.

In the present application, the term "stress relaxation behavior" means the stress change behavior of the polymer over time when the step strain of the shear flow has been applied to the polymer.

The stress change behavior depends on the nature of the polymer. For example, when the polymer is a perfect elastic body having only elasticity, a stress is generated immediately after applying the step strain thereto, and the stress is maintained at a constant value without dissipation with time. On the other hand, when the polymer is a perfect viscous body having only viscosity, the stress dissipates and is completely relaxed as soon as the step strain is applied. In addition, when the polymer is a general viscoelastic body having elasticity and viscosity at the same time, if the strain is completed, the stress begins to dissipate, but the stress remains as much as the ratio of the retained elasticity.

Also, the stress change behavior depends on the structure of the polymer. For example, when the step strain of the shear flow has been applied to a polymer, the shape of the polymer is also deformed, and then in the course of the relaxation of the polymer through the stress relaxation behavior with time, the length and molecular weight distribution of the main chain and side chains in the polymer, and the hierarchical structure of the side chain can affect the stress change behavior.

In one example, in the case of a general linear polymer having no side chain, the longer the length of the main chain is, the larger the influence of the surrounding polymers is, and thus the time required for the relaxation can be increased. Furthermore, the wider the molecular weight distribution is, the more the polymers having large molecular weight are present, and thus the overall relaxation time can be increased. On the other hand, in the case of a polymer having a side chain, the relaxation time can be longer than that of the linear polymer because the main chain cannot be relaxed unless the side chain is relaxed. Also, when the number of side chains is large or the side chains have a complex structure present in various stages, the relaxation time of the polymer can be increased.

In one example, the prediction of the rheological properties from the stress relaxation behavior can be done using a Doi-Edwards numerical analysis model.

In one example, the rheological properties can be expressed by a storage elastic modulus (G') and a loss elastic modulus (G") with respect to changes in angular velocity, where the storage elastic modulus (G') and the loss elastic modulus (G") can be calculated using a Doi-Edwards numerical analysis model.

Specifically, according to the Doi-Edwards numerical analysis model, a stress relaxation elastic modulus G(t) over time can be calculated by Equation 1 below disclosed in R. G. Larson, Macromolecules 2001, 34, 4556-4571.

[Equation 1]

$$G(t)/G_N^0 = 2\int_0^1 \exp(-t/t')\varphi(t')d\varphi(t')$$

In Equation 1 above, $G_N^0$ is a plateau modulus of the polymer, t' is a relaxation time of the polymer, and $\varphi$ represents a volume ratio of the un-relaxed polymer.

Also, from Equation 1 above, the storage elastic modulus (G') and the loss elastic modulus (G") over time can be calculated by Equations 2 and 3 below.

$$G'(\omega)/G_N^0 = 2\int_0^1 \frac{\omega^2 t'^2}{1+\omega^2 t'^2}\Phi(t')d\Phi(t') \quad \text{[Equation 2]}$$

$$G''(\omega)/G_N^0 = 2\int_0^1 \frac{\omega t'}{1+\omega^2 t'^2}\Phi(t')d\Phi(t') \quad \text{[Equation 3]}$$

In Equations 2 and 3 above, $\omega$ represents an angular velocity (angular frequency, [rad/s]) of the strain applied to the polymer. In addition, the method of the present application can further apply a McLeish-Larson Pom-Pom model to apply the branched polymers to the Doi-Edwards numerical analysis model.

The Pom-Pom model is a model in which a branched polymer structure is assumed as a polymer having a plurality of side chains at both ends of one main chain as in FIG. 2. In addition, the Pom-Pom polymer of FIG. 2 can be simulated as a linear polymer by adjusting the number and shape of a plurality of side chains at both ends.

In the step (c), the comparison between the predicted rheological property values of the polymer and the measured rheological property values of the polymer may be made by calculating an error value ($\varepsilon$) between the predicted rheological property value of the polymer and the measured rheological property value of the polymer and checking whether the error value ($\varepsilon$) is less than a predetermined error reference value ($\varepsilon_s$).

In one example, the error reference value ($\varepsilon_s$) may be a value in which the difference from the measured value of the rheological property is determined within a range of 0.1% to 10%, preferably within a range of 0.1% to 5%, but is not limited thereto.

With regard to the determination of the structural parameter value of the polymer in the step (c), when the error value is less than a predetermined error reference value, the random value assigned in the step (B) may be a definite value of the polymer structure parameter.

In one example, the quantitative analysis method of the polymer structure may be performed by repeating the step (B) and the step (C), for example, so that the number of the definite values can be derived in a range of 10 to 100. If the number of the definite values is less than 10, reliability with respect to the average value may be lowered due to a small number of samples, whereas if the number of the definite values exceeds 100, the average value converges and thus there is no difference from the average value of 100 definite values.

The definite value may have a range expressed by the minimum value and the maximum value of a plurality of definite values derived by repeating the step (B) and the step (C) two or more times. In another example, the definite value may have an average value for a plurality of definite values derived by repeating the step (B) and the step (C) two or more times.

Also, the step (A) may further comprise a step of measuring the molecular weight distribution of the polymer, where the method capable of measuring the molecular weight distribution is not particularly limited, and for example, GPC may be used.

Furthermore, the step (C) may further comprise a step of predicting the molecular weight distribution of the polymer to which the random value is assigned, and comparing the predicted molecular weight distribution value of the polymer with the measured molecular weight distribution value of the polymer to determine the value of the structural parameter of the polymer.

The prediction of the molecular weight distribution of the polymer can be made by assuming a log normal distribution on the polymer to which the random value is assigned.

In one example, the molecular weight distribution prediction can be predicted by Equation 4 below.

$$P(M) = \frac{1}{M\sqrt{2\pi\mu}}\exp\left(-\frac{(\ln M - \mu)^2}{2\sigma^2}\right) \quad \text{[Equation 4]}$$

In Equation 4 above, P(M) is a probability that a polymer having a molecular weight of M exists, $\sigma^2$ is a logarithm value of polydispersity index (PDI) of the main chain, and $\mu$ represents a median value of the molecular weight distribution. The median value of the molecular weight distribution means the difference between the logarithm value of the weight average molecular weight of the main chain and ½ of the logarithm value of the polydispersity index (PDI) of the main chain.

In the present application, the detailed description of the process of comparing the predicted molecular weight distribution value of the polymer with the measured molecular weight distribution value of the polymer and the process of deriving the definite value is the same as the process of the rheological property described above.

By using the molecular weight distribution of the polymer together with the above-described rheological properties of the polymer, the quantitative analysis method of a polymer structure according to the present application can obtain a result value closer to the actual polymer structure parameter than the polymer structure parameter value obtained using only rheological properties.

The present application relates to a computer-readable recording medium comprising a program capable of performing the quantitative analysis method of the polymer.

The computer-readable recording medium may comprise a program for executing the quantitative analysis method of the polymer structure.

The present application relates to an analyzer for performing the quantitative analysis method of the polymer structure. The analyzer provides a quantitative analyzer of a polymer structure comprising:

a first measuring part for measuring rheological properties of a polymer;

a setting part for selecting any one of structural parameters of the arbitrarily selected polymer and assigning a random value to the selected structural parameter;

a first predicting part for predicting the rheological property of the polymer to which the random value is assigned; and a calculating part for comparing the predicted rheological property value of the polymer with the measured value of the rheological property of the polymer to determine the value of the structural parameter of the polymer.

In addition, it may further comprise a second measuring part for measuring the molecular weight distribution of the polymer using GPC. Furthermore, the quantitative analyzer of a polymer structure according to the present application may further comprise a second predicting part for predicting the molecular weight distribution of the polymer to which the random value is assigned. The configurations or terms overlapping with the above-mentioned contents are the same as the configurations or terms related to the analysis method and thus the description thereof is omitted.

Hereinafter, the present invention will be described in detail through examples. However, the scope of protection of the present invention is not limited by the examples described below.

EXAMPLES

Experimental Example 1: Validation Through Structural Analysis of Linear Polymer Mixture (1) Measurement of Rheological Properties and Molecular Weight Distribution of Linear Polymer Mixture A polystyrene (PS) mixed solution was prepared by a liquid phase mixing method in which polystyrene (PS) 300K (weight average molecular weight: 300,000, PDI 3.79) and polystyrene (PS) 120K (weight average molecular weight: 120,000, PDI 2.98), two linear polymers knowing a weight average molecular weight and polydispersity index, were each dissolved in THF (tetrahydrofuran), then mixed at a ratio of 1:1 and stirred.

The polystyrene (PS) mixed solution was poured into n-hexane, precipitated and then separated to prepare a polystyrene (PS) polymer mixture. Rheological properties of the prepared polystyrene (PS) polymer mixture were measured using a rotational rheometer. Furthermore, the molecular weight distribution was measured using GPC.

(2) Prediction of Rheological Properties and Molecular Weight Distribution of Linear Polymer Mixture

TABLE 1

| Polystyrene (PS) 300K | | | Polystyrene (PS) 120K | | |
|---|---|---|---|---|---|
| Structural parameter | | | | | |
| Mw | PDI | Wt (%) | Mw | PDI | Wt (%) |
| Random value | | | | | |
| 100K~500K | 1~10 | 10~90 | 100K~500K | 1~10 | 10~90 |

Mw: weight average molecular weight,
PDI: polydispersity index,
Wt: weight ratio of each polymer in polymer mixture,
K: 1,000 units The random values were set within the numerical ranges of Table 1, and the rheological properties of the polystyrene (PS) mixture were predicted according to the Doi-Edwards numerical analysis model. Also, the molecular weight distribution was predicted according to the above-mentioned Equation 4. Then the measured values of the rheological properties and the molecular weight distribution of the polystyrene (PS) mixture measured in the above (1) were each compared with the predicted values of the rheological properties and the molecular weight distribution of the polystyrene (PS) mixture, and the results are shown in FIGS. 3 and 4.

In FIGS. 3 and 4, a value in which the error range of the measured value and the predicted value was less than 5% was derived as the definite value. In addition, from the setting of the random value, the process of deriving the definite value by comparing the measured value and the predicted value of the rheological property was repeated to derive 70 definite values. The ranges expressed by the minimum values and the maximum values of the above-derived definite values were shown in Table 2 below.

TABLE 2

| | Polystyrene (PS) 300K | | | Polystyrene (PS) 120K | | |
| --- | --- | --- | --- | --- | --- | --- |
| | Structural parameter | | | | | |
| | Mw | PDI | Wt (%) | Mw | PDI | Wt (%) |
| Definite value | 288K~339K | 2~2.4 | 45.5~55.5 | 102K~144K | 3.4~4.5 | 45.5~55.5 |
| Measured value | 300K | 3.79 | 50 | 120K | 2.98 | 50 |

Measured value: actual structural parameter value measured using an analyzer,
Error range: error of definite value to measured value,
Mw: weight average molecular weight,
PDI: polydispersity index,
Wt: weight ratio of each polymer in polymer mixture,
K: 1,000 units From Table 2 above, it can be confirmed that the definite values derived by the quantitative analysis method of the polymer structure according to the present application have very similar values to the measured values of the structural parameters of the polystyrene (PS) mixture. In the case of the PDI among the above structural parameters, there is a difference between the measured value and the definite value, but this difference is an error to occur because in the case of the actual polymer, the value of the PDI increases toward a specific value depending on the polymerization method or condition and simultaneously represents an asymmetric value, whereas the predicted value of the structural parameter according to the present application is calculated in bilateral symmetry upon predicting the PDI. Such an error is considered together with the calculated structural parameters, for example, the molecular weight or the weight ratio, and as shown in FIG. 3, the predicted value of the molecular weight distribution value for the entire mixture can be confirmed to a reliable level with respect to the measured value.

Experimental Example 2: Comparison of Polymer Mixture Structure Analysis Result by the Conventional Analyzer and the Analysis Method of the Present Application (1) Catalyst Preparation
Production of Catalyst (A) for Synthesizing Low Molecular Weight Linear Polymer

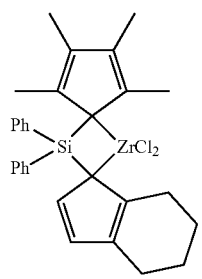

Catalyst A (a) TMCP-Li (1.3 g, 10 mmol), CuCN (45 mg, 5 mol %) and THF (10 mL) were poured into a 250 mL Schlenk flask. Dichlorodiphenylsilane (2.5 g, 10 mmol) was added dropwise thereto at −20° C. or lower, and then the mixture was stirred at room temperature for 16 hours. The temperature was lowered to −20° C. and indene-lithium (indene-Li, 1.2 g, 10 mmol in 10 mL of THF) was added dropwise thereto. The mixture was stirred at room temperature for 24 hours and dried in a vacuum to remove the solvent. The residue was filtered with hexane to remove LiCl, and in the filtrate, hexane was dried in a vacuum to obtain an intermediate.

The prepared intermediate (4.2 g, 10 mmol) and THF (15 mL) were poured into a 100 mL Schlenk flask and the temperature was lowered to −20° C. N-Butyl lithium (n-BuLi, 2.5 M in hexane, 8.4 mL, 21 mmol) was slowly added dropwise and stirred at room temperature for 6 hours. $ZrCl_4(THF)_2$ (3.8 g, 10 mmol) and toluene (15 mL) were poured into a 250 mL Schlenk flask and stirred at −20° C. or lower. The lithiated ligand solution was slowly added thereto. After stirring the mixture at room temperature for 48 hours, the solvent was removed by drying in a vacuum. The residue was dissolved in dichloromethane and filtered to remove lithium chloride (LiCl), and then dichloromethane was dried in a vacuum. 30 mL of toluene was added thereto, stirred for 16 hours, and then filtered to obtain an intermediate as a lemon color solid (2.1 g, 3.6 mmol, yield 36%).

$^1$H NMR (500 MHz, $CDCl_3$): 8.08-8.12 (m, 2H), 7.98-8.05 (m, 2H), 7.77 (d, 1H), 7.47-7.53 (m, 3H), 7.42-7.46 (m, 3H), 7.37-7.41 (m, 2H), 6.94 (t, 1H), 6.23 (d, 1H), 1.98 (s, 3H), 1.95 (s, 3H), 1.68 (s, 3H), 1.52 (s, 3H).

(b) The intermediate (1.0 g, 1.7 mmol) finally prepared in (a) above, Pd/C (10 mol %) and dichloromethane (40 mL) were injected into a 100 mL high-pressure reactor, and $H_2$ (60 bar) was charged, followed by stirring at 80° C. for 24 hours. At the end of the reaction, the reactant was passed through a celite pad to remove the solid, thereby obtaining catalyst A (0.65 g, 1.1 mmol, yield 65%).

$^1$H NMR (500 MHz, $CDCl_3$): 7.90-8.00 (m, 4H), 7.38-7.45 (m, 6H), 6.80 (s, 1H), 5.71 (s, 1H), 3.50-3.15 (m, 1H), 2.75-2.85 (m, 1H), 2.50-2.60 (m, 1H), 2.12 (s, 3H), 2.03 (s, 3H), 1.97-2.07 (m, 1H), 1.76 (s, 3H), 1.53-1.70 (m, 4H), 1.48 (s, 3H).

Catalyst (B) for Synthesizing a High Molecular Weight Linear Polymer

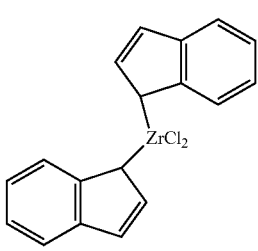

Catalyst B

It was purchased from Strem (CAS No.: 12148-49-1).

(2) Catalyst Supporting Method:

To a 10 L high-pressure reactor, 4.0 kg of toluene solution was added and 800 g of silica (Grace Davison, SP2410) was introduced, and then stirred while raising the temperature of the reactor to 40° C.

1.5 kg of a 30 wt % methylaluminoxane (MAO)/toluene solution (Albemarle) was introduced, the temperature was raised to 80° C., and then the mixture was stirred at 200 rpm for 12 hours. Catalyst A and Catalyst B were introduced into a 2 L Schlenk flask at a ratio of 7.4 g:4.9 g, 7.4 g:9.8 g, 7.4 g:19.6 g, and 7.4 g:0 g, respectively, 25 g of butyl aluminum was added to 1 L of toluene and reacted at 40° C. for 60 minutes, and then the reaction mixture was introduced into the high-pressure reactor, the temperature was raised to 80° C., and then the mixture was stirred for 2 hours. After lowering the reactor temperature to room temperature, the stirring was stopped, and the mixture was allowed to stand for 30 minutes and then decanted. To the reactor, 3.0 kg of hexane was introduced and the hexane slurry solution was transferred to a filter dryer and filtered. After purging with 1.5 bar of argon for 10 minutes, four mixed catalysts of Table 3 below were prepared by drying the mixtures under a vacuum at 40° C. for 3 hours.

TABLE 3

|  | Mixed catalyst 1 | Mixed catalyst 2 | Mixed catalyst 3 | Mixed catalyst 4 |
| --- | --- | --- | --- | --- |
| Catalyst A content (g) | 7.4 | 7.4 | 7.4 | 7.4 |
| Catalyst B content (g) | 4.9 | 9.8 | 19.6 | 0 |

(3) Production of Sample for Structural Analysis

Samples for the structural analysis were low density polyethylene and a continuous polymerization reactor, which is a slurry loop process of isobutene, was used as a polymerization reactor, where the reactor volume was 140 L and the reaction flow rate was operated at about 7 m/s. All gas streams (ethylene and hydrogen) and 1-hexene, which is a comonomer, required for the polymerization were continuously introduced, where the individual flow rates were adjusted as needed. The concentrations of all gas streams and 1-hexene, which is a comonomer, were confirmed by on-line gas chromatography. Each of the catalysts prepared above was used as a catalyst, and the isobutene slurry was introduced thereto. The reactor pressure was maintained at 40 bar and the polymerization temperature was 84° C. The specific polymerization conditions were as shown in Table 4 below.

TABLE 4

|  | Sample 1 | Sample 2 | Sample 3 | Sample 4 |
| --- | --- | --- | --- | --- |
| Mixed catalyst | Mixed catalyst 1 | Mixed catalyst 2 | Mixed catalyst 3 | Mixed catalyst 4 |
| Ethylene inflow | 25 | 24 | 24 | 23 |
| Hydrogen input | 8 | 20 | 5 | 8 |
| Hexane input | 9.2 | 10.1 | 8.9 | 8.8 |
| Slurry density | 550 | 545 | 550 | 554 |
| Activity | 4.1 | 4.4 | 4.9 | 3.8 |
| Bulk density | 0.40 | 0.39 | 0.41 | 0.39 |
| Setting efficiency | 50 | 49 | 53 | 52 |

<Unit> Ethylene inflow: kg/hr, Hydrogen and hexane input: ppm, Slurry density: g/L, Activity: kg-PE/kg-SiO$_2$/hr, Bulk density: g/mL, Setting efficiency: %

(4) Comparison of Structural Analysis Results

Analysis Results of the Polymer Mixture Structure by the Conventional Analyzer

For Samples 1 to 4 above, the measured data of number average molecular weights, weight average molecular weights and polydispersity indexes are shown in Table 5 below, which are measured at 160° C. by dissolving each sample in 1,2,4-trichlorobenzene containing 0.0125% BHT at 160° C. for 10 hours to be subjected to pretreatment and using PL-S260 from Agilent Technology, a conventional analyzer.

TABLE 5

| Structural parameter |  | Mn | Mw | PDI |
| --- | --- | --- | --- | --- |
| Measured value | Sample 1 | 30,761 | 99,135 | 3.2 |
|  | Sample 2 | 31,797 | 95,754 | 3.0 |
|  | Sample 3 | 36,135 | 102,203 | 2.8 |
|  | Sample 4 | 40,300 | 102,400 | 2.5 |

Analysis Results of the Polymer Mixture Structure by the Analysis Method of the Present Application For Samples 1 to 4 above, rheological properties and molecular weight distribution were measured using a rotational rheometer and GPC. Then, the weight ratio (Wt), the weight average molecular weight (Mw) and the number of side chains of each polymer in the polymer mixture were selected as the structural parameters of the four samples, and random values of the selected structural parameters were set. Thereafter, the rheological properties and the molecular weight distribution were predicted from the random values using the polymer structure analysis method according to the present invention. A random value having an error value between the predicted value and the measured value of less than 5% was derived as a definite value, and 70 definite values were again derived by repeating from the process of setting a random value to the process of comparing the predicted value and the measured value of the rheological property to derive a definite value. The ranges expressed by the minimum values and the maximum values of the derived definite values were shown in Table 6 below.

TABLE 6

|  |  | Low molecular weight linear structure polymer | | High molecular weight linear structure polymer | | Branched structure polymer | | | |
| --- | --- | --- | --- | --- | --- | --- | --- | --- | --- |
|  |  | Structural parameter | | | | | | | |
|  |  | Wt (%) | Mw | Wt (%) | Mw | Wt (%) | Main chain Mw | Side chain Mw | Number of side chains |
| Definite value | Sample 1 | 22.0 ± 6.8 | 33K ± 10K | 47.2 ± 7.1 | 61K ± 7K | 30.9 ± 3.3 | 220K ± 28K | 48K ± 20K | 0.046 |

TABLE 6-continued

|  | Low molecular weight linear structure polymer | | High molecular weight linear structure polymer | | Branched structure polymer | | | |
|---|---|---|---|---|---|---|---|---|
|  | Structural parameter | | | | | | | |
|  | Wt (%) | Mw | Wt (%) | Mw | Wt (%) | Main chain Mw | Side chain Mw | Number of side chains |
| Sample 2 | 13.3 ± 6.0 | 26K ± 10K | 54.2 ± 8.0 | 61K ± 6K | 32.7 ± 4.0 | 202K ± 24K | 43K ± 24K | 0.043 |
| Sample 3 | 17.2 ± 4.5 | 31K ± 8K | 49.8 ± 8.0 | 75K ± 8K | 33.2 ± 6.3 | 202K ± 26K | 44K ± 26K | 0.041 |
| Sample 4 | 9.7 ± 5.4 | 29K ± 13K | 61.8 ± 7.3 | 91K ± 11K | 28.5 ± 4.6 | 160K ± 20K | 28K ± 15K | 0.047 |

Number of side chains: number of side chains present in a carbon number of 1000,
Wt: weight ratio of each polymer in polymer mixture Tables 5 and 6 above show that the analysis using the existing analyzer can only measure the structural parameter values of the entire polymer mixture, but the structural parameters for each of low molecular weight linear structures, high molecular weight linear structures and branched polymer structures cannot be known. On the other hand, when using the quantitative analysis method of the polymer structure according to the present application, the tables show that the structural parameter values can be quantitatively analyzed for each of low molecular weight linear structure, high molecular weight linear structure and branched structure polymers mixed in the polymer mixture.

The invention claimed is:

1. A method for quantitative analysis of a polymer structure comprising:
   (A) measuring rheological properties of the polymer;
   (B) selecting one or more parameters among structural parameters of said polymer, and assigning random values to said selected structural parameters; and
   (C) predicting rheological properties of the polymer to which the random values are assigned, and comparing said predicted rheological property values of the polymer with the measured rheological property values of the polymer to determine structural parameters values of the polymer,
   wherein in the step (C), a step strain of a shear flow is applied to the polymer to which the random value is assigned, where the rheological properties are predicted from a stress relaxation behavior of the polymer induced by said step strain, and
   wherein the predicting of the rheological properties of the polymer is done using a Doi-Edwards numerical analysis model.

2. The method for quantitative analysis of a polymer structure according to claim 1, wherein the step (A) is performed by a rheometer.

3. The method for quantitative analysis of a polymer structure according to claim 1, wherein in the step (A), the polymer is at least one selected from the group consisting of a linear polymer, a branched polymer, a linear polymer mixture and a branched polymer mixture.

4. The method for quantitative analysis of a polymer structure according to claim 3, wherein the branched polymer has a weight average molecular weight ratio of side chains to the main chain of 40% or less, or a weight average molecular weight in only the side chains of 3,000 or more.

5. The method for quantitative analysis of a polymer structure according to claim 3, wherein the structural parameter selected in the step (B) is one or more selected from a shape of the polymer; a weight average molecular weight (Mw) of the main chain or side chains; a polydispersity index (PDI) of the main chain or side chains; or a number of the side chains.

6. The method for quantitative analysis of a polymer structure according to claim 5, wherein, when the polymer selected in the step (A) is a polymer mixture, said structural parameter further comprises a mass fraction between the mixed polymers.

7. The method for quantitative analysis of a polymer structure according to claim 1, wherein the comparison, which is performed in the step (C), between said predicted rheological property values of the polymer and said measured rheological property values of the polymer is made by calculating an error value ($\varepsilon$) between the predicted rheological property value of the polymer and the measured rheological property value of the polymer and checking whether said error value ($\varepsilon$) is less than a predetermined error reference value ($\varepsilon_s$).

8. The method for quantitative analysis of a polymer structure according to claim 7, wherein the determination of the structural parameter values of the polymer in the step (C) is made by setting the random value assigned in the step (B) as a definite value, when said error value is less than a predetermined error reference value ($\varepsilon_s$).

9. The method for quantitative analysis of a polymer structure according to claim 8, wherein the step (B) and the step (C) are repeated.

10. The method for quantitative analysis of a polymer structure according to claim 9, wherein a definite value is expressed by the minimum value and the maximum value of a plurality of definite values derived by repeating said step (B) and said step (C) two or more times.

11. The method for quantitative analysis of a polymer structure according to claim 9, wherein said definite value is expressed by an average value of a plurality of definite values derived by repeating said step (B) and said step (C) two or more times.

12. The method for quantitative analysis of a polymer structure according to claim 1, wherein the step (A) further comprises measuring a molecular weight distribution of the polymer using GPC.

13. The method for quantitative analysis of a polymer structure according to claim 12, wherein the step (C) further comprises predicting the molecular weight distribution of the polymer to which the random value is assigned, and comparing said predicted molecular weight distribution value of the polymer with the measured molecular weight distribution value of the polymer to determine a value of the structural parameter of the polymer.

14. The method for quantitative analysis of a polymer structure according to claim 13, wherein the prediction of the molecular weight distribution of the polymer is made by assuming a log normal distribution on the polymer to which the random value is assigned.

15. A computer-readable recording medium, wherein a program for executing the method of claim 1 is recorded.

* * * * *